United States Patent [19]
Wilk

[11] Patent Number: 5,533,958
[45] Date of Patent: Jul. 9, 1996

[54] INTRAPERICARDIAL ASSIST DEVICE AND ASSOCIATED METHOD

[76] Inventor: Peter J. Wilk, 185 West End Ave., New York, N.Y. 10023

[21] Appl. No.: 286,817

[22] Filed: Aug. 5, 1994

Related U.S. Application Data

[63] Continuation-in-part of Ser. No. 78,567, Jun. 17, 1993, Pat. No. 5,385,528.

[51] Int. Cl.$^6$ ................................................ A61B 17/12
[52] U.S. Cl. ........................... 600/18; 601/153; 604/99
[58] Field of Search .................... 601/151, 152, 601/153; 607/5, 129, 130, 116, 119; 600/16, 17, 18; 128/639, 644; 604/96, 97, 98, 99

[56] References Cited

U.S. PATENT DOCUMENTS 3,587,567  6/1971  Schiff ..................................... 601/153
5,169,381  12/1992  Snyders .................................. 601/153

*Primary Examiner*—William E. Kamm
*Assistant Examiner*—Scott M. Getzow
*Attorney, Agent, or Firm*—R. Neil Sudol; Henry D. Coleman

[57] ABSTRACT

An intrapericardial assist device and method comprises an electrode carrier in the form of an inflatable cuff-shaped balloon adapted for juxtaposition to a patient's heart in an intrapericardial space. An electrical contact or electrode is disposed on the contact surface of the carrier for conducting electrical energy to the heart upon an insertion of the electrode carrier into the intrapericardial space and upon inflation of the balloon so that the electrode engages cardiac tissues.

19 Claims, 3 Drawing Sheets

INTRAPERICARDIAL ASSIST DEVICE AND ASSOCIATED METHOD

CROSS-REFERENCE TO RELATED APPLICATION

This application is a continuation-in-part of application Ser. No. 08/078,567 filed Jun. 17, 1993, now U.S. Pat. No. 5,385,528.

BACKGROUND OF THE INVENTION

This invention relates to an intrapericardial assist device. This invention also relates to an associated surgical method of starting a stopped heart or restarting a heart with a pronounced arrythmia.

When a patient's heart stops, for example, in the operating room, cardiopulmonary resuscitation (CPR) is required. In that procedure the chest is violently pounded at the region of the sternum to compress the chest and thereby compress the heart between the sternum and the spine. This compression forces blood out of the ventricles through the one-way valves of the heart. When the pressure on the heart is released, the heart expands and blood is sucked into the heart.

For all its violence, CPR is a delicate procedure in that it must be performed correctly in order to have the desired result of starting the stopped heart. A problem with CPR is that, whether or not it is performed correctly, CPR invariably results in cracked ribs, a fractured sternum and destroyed costochondral (cartilage) junctions. Thus even if a patient survives CPR, he is usually injured.

It is known to insert a needle into the intrapericardial space around the heart. This procedure is frequently undertaken to obtain a sample of fluid (e.g., blood) in the intrapericardial space. An electrical sensor at the tip of the needle senses when the surface of the heart has been reached and alerts the doctor to cease pushing on the needle.

OBJECTS OF THE INVENTION

An object of the present invention is to provide a method and/or an associated device for resuscitating a stopped heart.

A more particular object of the present invention is to provide such a method wherein the excessive trauma characteristic of conventional CPR is largely, if not completely, obviated.

Another object of the present invention is to provide such a method which is easy and quick to use.

Another, more particular, object of the present invention is to provide such a method which may be implemented at least partially automatically, thereby reducing the exertion required by the resuscitating personnel.

Yet another object of the present invention is to provide a method for introducing or instilling a regular heart beat into a heart which has a pronounced and potentially fatal arrythmia.

A further particular object of the present invention is to provide a device for cardiopulmonary resuscitation and/or for regularizing a heart beat.

These and other objects of the present invention will be apparent from the drawings and detailed descriptions herein.

SUMMARY OF THE INVENTION

An intrapericardial assist device comprises, in accordance with the present invention, an electrode carrier adapted for juxtaposition to a patient's heart in an intrapericardial space, the electrode carrier having a surface adapted for contact with the patient's heart. An electrical contact or electrode is disposed on the contact surface of the carrier for conducting electrical energy to the heart upon an insertion of the electrode carrier into the intrapericardial space. Current transmission elements are operatively connected to the electrical contact for supplying electrical energy to the electrical contact, while means are connected to the electrode carrier for maintaining the contact surface of the electrode carrier in contact with the patient's heart.

According to another feature of the present invention, the electrode carrier is a collapsible member which has a configuration of a slotted cuff in an expanded configuration. The electrode carrier has a predetermined size and shape in the expanded configuration so that the electrode carrier is disposable in the intrapericardial space in juxtaposition to the patient's heart. Preferably, one or more spring elements, e.g., in the form of elongate ribs, are connected to the electrode carrier for automatically unfurling the carrier from a folded collapsed configuration to the expanded configuration.

According to a further feature of the present invention, the electrode carrier takes the form of a balloon, which may in turn take the form of a cuff. The means for maintaining the contact surface of the electrode carrier in contact with the patient's heart includes inflation componentry operatively connected to the electrode carrier for inflating the electrode carrier from a folded collapsed configuration to an unfolded expanded configuration.

Advantageously, the inflation componentry includes means for automatically and periodically inflating and alternately deflating the balloon upon a disposition thereof into the intrapericardial space.

According to a supplemental feature of the present invention, a sensor is disposed in part on the electrode carrier for generating an electrocardiograph of the patient's heart activity. This sensor or sensor array facilitates the monitoring of heart activity during a heart resuscitation or beat regularization procedure.

A surgical method for resuscitating a stopped heart comprises, in accordance with the present invention, the steps of (a) providing an inflatable balloon in a collapsed configuration, the balloon being provided with an electrode on a surface adapted for contact with a patient's heart, (b) inserting the balloon into an intrapericardial space about the patient's heart, (c) inflating the balloon to place the electrode in electrically conductive contact with the heart of the patient upon insertion of the balloon into the intrapericardial space, and (d) conducting a voltage through the electrode to the patient's heart upon inflation of the balloon.

In accordance with another feature of the present invention, the voltage conducted to the patient's heart is a defibrillating voltage and the methodology further comprises the steps of (e) monitoring heart action via an EKG device for a predetermined period upon conduction of the voltage to the heart, and (f) inflating the balloon in synchronism with a heart contraction, upon a determination that the heart has started with an inadequate strength, to place a compressive pressure on the heart to thereby increase pumping action. In another step (g), the balloon is at least partially deflated upon completion of the voltage conduction and prior to the monitoring of the heart action. The EKG monitor may be a conventional EKG device separate from the balloon and electrode assembly. Alternatively, the heart action may be monitored via sensing electrodes attached to the balloon at the contact surface thereof.

In accordance with a further feature of the present invention, the method also comprises the additional steps of (h)

generating a pacemaker type periodic voltage, (i) applying the periodic voltage to the heart via the electrode upon inflating the balloon to place a compressive pressure on the heart, and (j) maintaining the balloon in an inflated state during the application of the pacemaker type periodic voltage, to maintain the electrode in electrically conductive contact with the heart of the patient. In some cases, the pacemaker type periodic voltage may be applied to the heart independently of any other heart treatment as described herein. Thus, the pacemaker voltage may be applied even where a defibrillating voltage and/or compressive periodic balloon inflation is not necessary.

In accordance with yet another feature of the present invention, the insertion of the balloon into the intrapericardial space is implemented using a hypodermic type needle. The needle is inserted through a skin surface and into the intrapericardial space, the balloon being injected in the collapsed configuration through the needle into the intrapericardial space.

In accordance with a more particular feature of the present invention, a dilating device is provided for facilitating the insertion of the balloon into the intrapericardial space. The needle is partially inserted through the skin surface and into the intrapericardial space and a distal end portion of the dilating device is placed into the intrapericardial space via the needle upon the partial insertion thereof into the intrapericardial space. The method also comprises the step of expanding the dilating device upon the insertion of the distal end portion thereof into the intrapericardial space, the balloon being subsequently inserted into the intrapericardial space through the expanded dilating device.

A method in accordance with the present invention solves the problem of the trauma and injury inflicted upon a patient during conventional CPR. Ribs and sternum remain intact.

A method and apparatus in accordance with the present invention serves in part to introduce a regular heart beat into a heart which has a pronounced and potentially fatal arrythmia. Pursuant to the present invention, upon insertion of the electrode-carrying balloon into the intrapericardial space, the arrythmic heart is shocked by a defibrillating voltage into exhibiting a more regular heart beat. The balloon is then used to assist the heart during initial stages of its newly regular action. A pacemaker voltage is subsequently applied to the restarted heart for extending the regular action of the heart.

DETAILED DESCRIPTION

Figure 1:
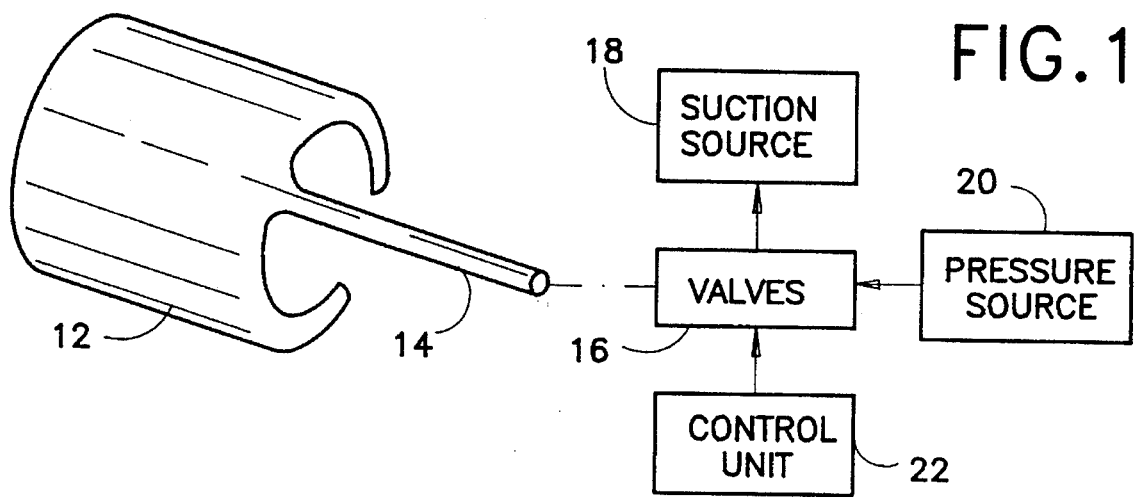
FIG. 1 is partially a schematic perspective view, on a reduced scale, and partially a block diagram of an intrapericardial assist or resuscitation assembly in accordance with the present invention, showing an inflatable intrapericardial cuff in an expanded configuration.

As illustrated in FIG. 1, an intrapericardial assist or resuscitation assembly comprises an alternately inflatable and collapsible balloon 12 in the form of a cuff. Cuff 12 has an elongate tube 14 extending to a valve device 16 which is connected to a suction source or vacuum generator 18 and to a source 20 of pressurized fluid such as water, saline solution or a gas such as air. In response to signals from a control unit 22, valve device 16 periodically connects cuff 12 to pressure source 20 and alternately to suction source 18, whereby cuff 12 is rapidly and forcefully inflated with a predetermined periodicity.

Control unit 22 may be provided with setting knobs (not illustrated) for varying the rate and maximum pressure that is applied to the cuff upon proper disposition thereof in the intrapericardial space about the heart.

Figure 2:
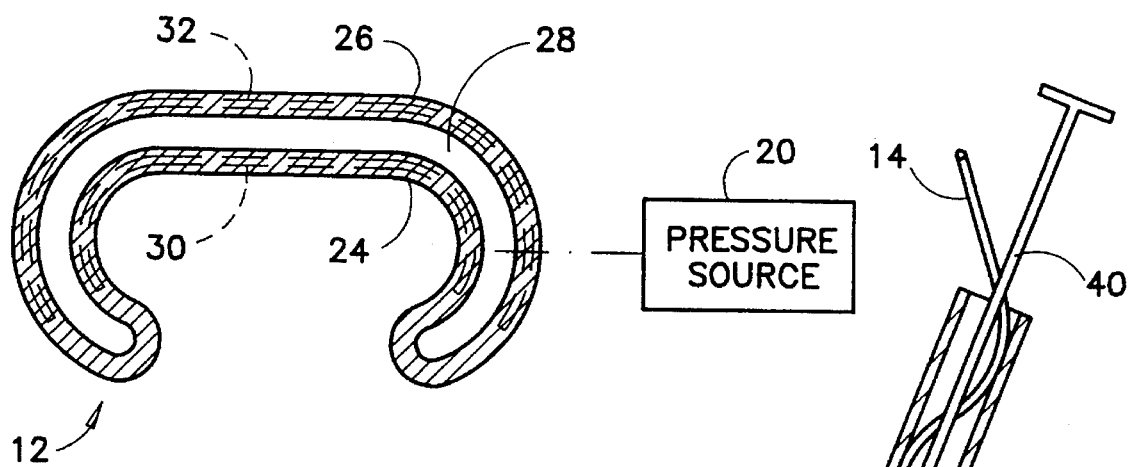
FIG. 2 is a schematic cross-sectional view of the inflatable intrapericardial cuff of FIG. 1.

As illustrated in FIGS. 1 and 2, cuff 12 has an arcuate, generally C-shaped configuration in its expanded or inflated state. Cuff 12 has a pair of major C-shaped walls 24 and 26 defining a pressurization chamber 28. Embedded in walls 4 and 26 are spring elements or ribs 30 and 32 which can be bent into a curled configuration (see FIG. 3) but which tend to resume their C-shaped expanded configurations when cuff 12 is placed into an intrapericardial space during a cardiopulmonary resuscitation procedure.

Figure 3:
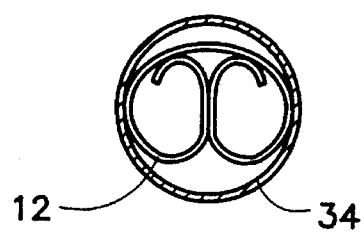
FIG. 3 is a schematic transverse cross-sectional view of the inflatable intrapericardial cuff of FIGS. 1 and 2 in a folded, collapsed pre-insertion configuration inside a hypodermic type needle.
Figure 4:
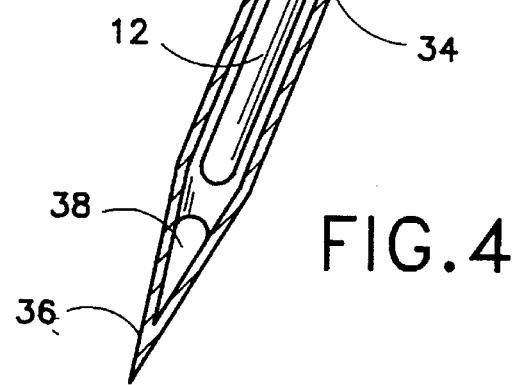
FIG. 4 is a schematic longitudinal cross-sectional view of the inflatable intrapericardial cuff of FIGS. 1–3 in the folded, collapsed pre-insertion configuration inside the hypodermic needle of FIG. 3.

As illustrated in FIGS. 3 and 4, prior to a cardiopulmonary resuscitation procedure, cuff 12 is folded and inserted in a collapsed configuration inside a hollow hypodermic type needle 34. Needle 34 is provided at a distal end 36 with an aperture 38 for the ejection of folded and collapsed cuff 12 by a distally directed stroke of a plunger member 40 upon a disposition of distal end 36 into an intrapericardial space during a cardiopulmonary resuscitation procedure. Distal end 36 is also provided with an electrical sensor for detecting the surface of the heart, as is conventional in known intrapericardial sampling needles.

Distal end 36 of intrapericardial needle 34 is inserted into the intrapericardial space through the skin under the patient sternum.

Figure 5:
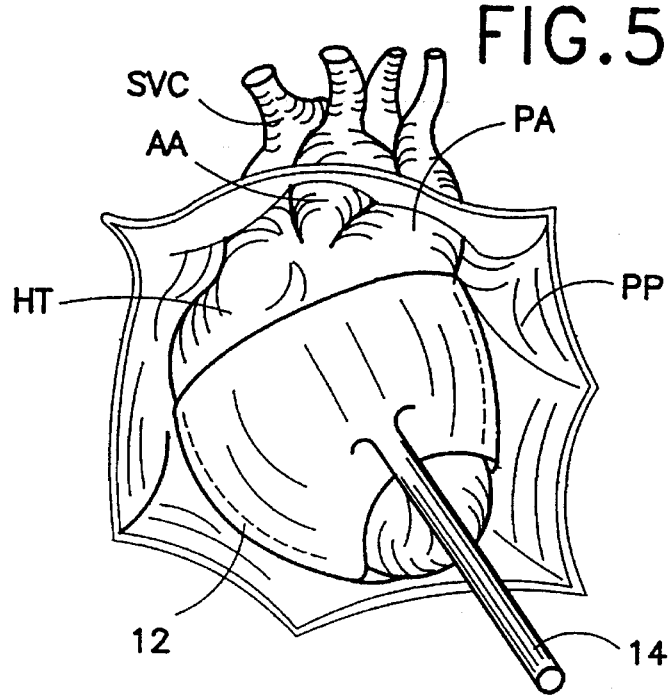
FIG. 5 is a perspective view of the cuff of FIGS. 1–4 in an expanded configuration in place inside an intrapericardial space.

FIG. 5 shows the placement of cuff 12 in an intrapericardial space between a heart HT and the associated surrounding parietal pericardium PP. The diagram also shows the superior vena cava SVC, the pulmonary artery PA, the ascending aorta AA, and other veins and arteries.

Figure 6:
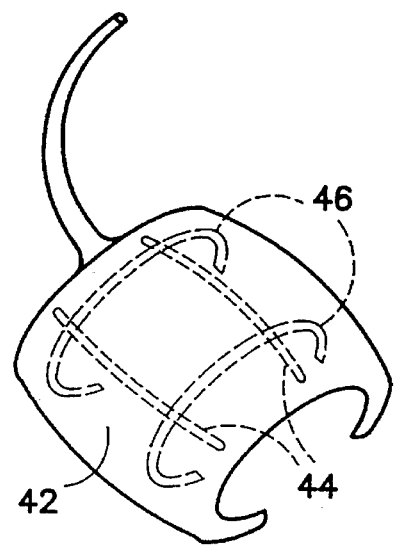
FIG. 6 is another schematic perspective view of an inflatable intrapericardial cuff in accordance with the present invention, showing memory ribs inside the cuff for aiding in an unfolding thereof upon insertion of the cuff into an intrapericardial space.

As depicted in FIG. 6, an inflatable intrapericardial cuff 42 may be provided with a plurality of longitudinally extending ribs 44 and a plurality of transversely extending expansion ribs 46. Each rib 46 has a memory whereby the rib may be bent for insertion and retrieval from a patient's intrapericardial space, but tends to assume a pre-established configuration (FIG. 6) upon insertion of the cuff 42 into an intrapericardial space or cavity.

Figure 7A:
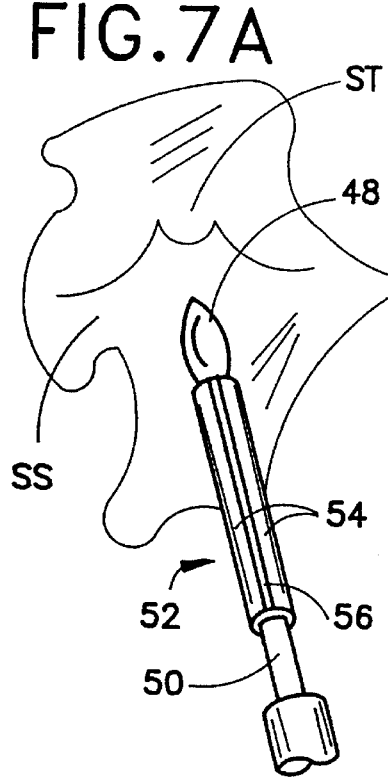
FIGS. 7A–7C are schematic perspective views showing successive steps in one intrapericardial cuff insertion procedure in accordance with the present invention.
Figure 7B:
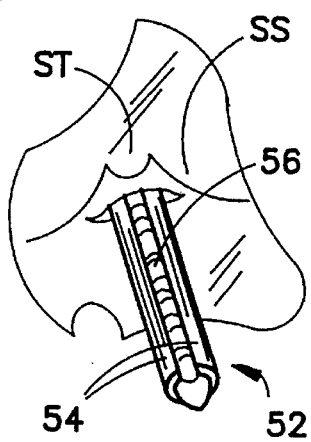
Figure 7C:
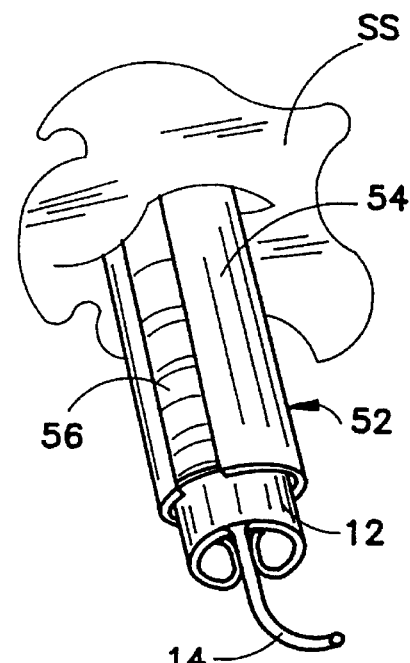

In another cuff insertion procedure depicted in FIGS. 7A–7C, a sharp distal tip 48 of an intrapericardial needle 50 is inserted through a patient's skin SS under the sternum ST. A dilating device 52 comprising a plurality of longitudinal ribs 54 interconnected by stretchable membranes 56 surrounds needle 50 during the insertion procedure. Upon the insertion of distal tip 48 into the intrapericardial cavity at the patient's heart, dilating device is slid in the distal direction so that a distal end portion thereof is disposed or inserted into the intrapericardial cavity. Needle 50 is then removed, as shown in FIG. 7B.

Upon the removal of needle 50 from the patient, leaving dilating device 52 partially inserted into the patient's intrapericardial cavity, the dilating device may be expanded, for example, by the insertion of a series of increasing large elongate rigid dilators (not shown). Then, cuff 12 or 42 is inserted in a folded collapsed configuration into the intrapericardial cavity through the expanded dilating device 52, as shown in FIG. 7C. An inserter (not illustrated) may be used for pushing the cuff through dilating device 52.

The general use and structure of dilating device 52 is described in detail in allowed U.S. patent application Ser. No. 851,097 filed Mar. 13, 1992 and U.S. patent application Ser. No. 893,991 filed Jun. 5, 1992. The disclosures of those applications are hereby incorporated by reference.

Figure 8:
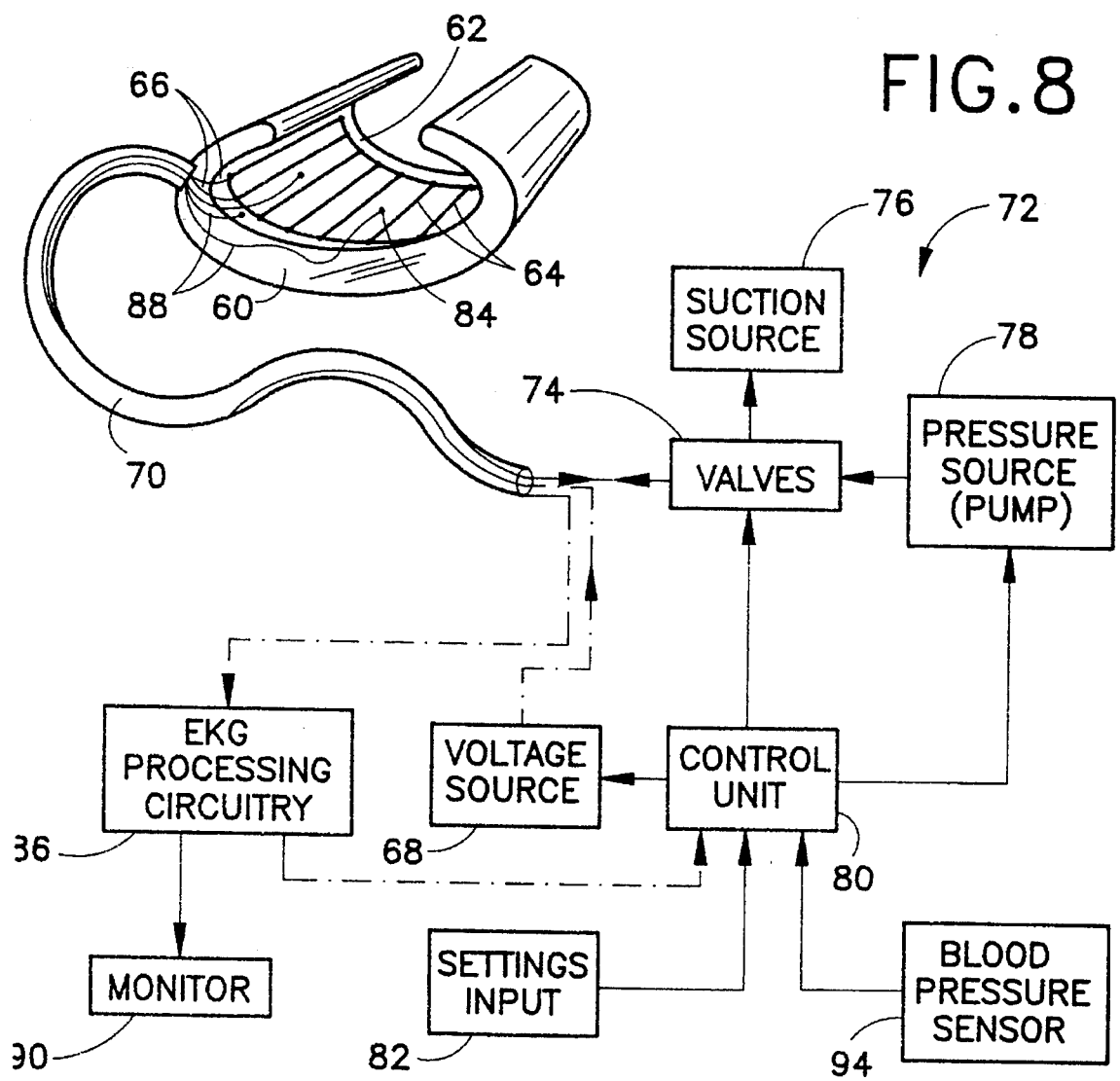
FIG. 8 is partially a schematic perspective view, on a reduced scale, and partially a block diagram of a modified intrapericardial assist or resuscitation assembly in accordance with the present invention, showing an expanded intrapericardial cuff with a voltage source operatively connected to an electrode array along an inner surface of the cuff.

As depicted in FIG. 8, an intrapericardial assist device comprises an electrode carrier in the form of an inflatable balloon 60 adapted for juxtaposition to a patient's heart in an intrapericardial space, as discussed hereinabove with reference to FIG. 5. The electrode-carrying balloon 60 has an inwardly facing surface 62 adapted for contact with the patient's heart. An array of electrical contacts or electrode wires 64 is disposed on contact surface 62 of balloon 60 for conducting electrical energy to the patient's heart upon an insertion of balloon 60 into the intrapericardial space. Current transmission elements or leads 66 are operatively connected to electrical contacts 64 for delivering electrical energy thereto from a voltage source 68. A hose 70 extends to balloon 60 for maintaining the balloon in an inflated state and thereby maintaining the balloon's contact surface 62 in adequate engagement with the patient's heart during the application of electrical energy to the heart via voltage source 68, transmission leads 66 and electrical contacts or electrodes 64.

Balloon 60 is a collapsible member with a configuration of a slotted cuff in an expanded configuration. Balloon 60 has a predetermined size and shape in the expanded configuration so that it is disposable in the intrapericardial space in juxtaposition to the patient's heart. Preferably, one or more spring elements in the form of elongate ribs, e.g. 30, 32 (FIG. 2) or 44, 46 (FIG. 6), are connected to balloon 60 for automatically unfurling the balloon from a folded collapsed insertion configuration to an expanded use configuration.

The means for maintaining contact surface 62 of balloon 60 in engagement with the patient's heart during a cardiac jump start as described herein includes inflation componentry 72 operatively connected to balloon 60 via hose 70. Inflation componentry 72 includes a valve device 74 which is connected to a suction source or vacuum generator 76 and to a source 78 of pressurized fluid such as water, saline solution or a gas such as air or carbon dioxide. In response to signals from a control unit 80 such as a specially programmed microprocessor, pressure source 78 and valve device 74 pressurize balloon 60 to a predetermined pressure during an electrical cardiac stimulation procedure, whereby contacts or electrodes 64 are maintained in electrically conductive contact with a patient's heart. Alternatively, during mechanical heart stimulation as described herein, control unit 80 activates valve device 74 to periodically connect balloon 60 to pressure source 78 and alternately to suction source 76, whereby balloon 60 is rapidly and forcefully inflated with a predetermined periodicity.

Control unit 80 is provided with setting knobs 82 for enabling a preselection of an inflation pressure of balloon 60 and for varying the rate and maximum pressure that is applied to balloon 60 upon proper disposition thereof in the intrapericardial space about the heart.

As further depicted in FIG. 8, a plurality of sensor electrodes 84 is disposed on contact surface 62 of balloon 60 for monitoring natural voltages of a cardiac cycle. Sensor electrodes 84 are connected to EKG processing circuitry 86 via leads 88. According to conventional signal processing techniques, circuitry 86 generates a signal indicative of the patient's heart activity and displays the signal via a cathode ray tube (CRT) or video screen 90. Sensor electrodes 84 and EKG processing circuitry facilitate the monitoring of heart activity during a heart resuscitation or beat regularization procedure as described below.

In a surgical method for reactivating a malfunctioning heart, e.g., a stopped heart or a dangerously arrythmic heart, balloon 60 is inserted into an intrapericardial space about the patient's heart, as discussed above with reference to FIGS. 5 and 7A–7C. Upon deployment of balloon 60 in the intrapericardial space, the balloon is inflated to place electrodes 64 in electrically conductive contact with the heart. Then, a defibrillating type voltage produced by a generator 92 of voltage source 68 is conducted via leads 66 and electrodes 64 to the patient's heart.

Upon the conduction of the defibrillating type voltage to the patient's heart, heart action is monitored via electrodes 84, processing circuitry 86 and CRT 90 for a predetermined period. If it is determined at that juncture that the patient's heart has started but with an insufficiently strong action, input provided to control unit 80 via setting knobs 82 induces that unit to control valve device 74 so as to inflate balloon 60 forcefully in synchronism with a heart contraction. Synchronism may be achieved, for instance, by providing control unit 80 with input from a blood pressure and pulse sensor 94 (including, e.g., a separate pressure cuff). Alternatively, if balloon 60 is sufficiently inflated, control unit 80 may receive input from EKG processing circuitry 86. In either case, control unit or micro-processor 80 determines when a heart contraction is about to occur and opens valve device 74 to induce a flow of pressurizing fluid along hose 70 to balloon 60. The placement of a compressive pressure on the heart to thereby increase pumping action may alternatively be initiated manually by providing a triggering signal to control unit 80 via setting knobs or input 82.

Balloon 60 may be at least partially deflated upon conduction of the defibrillating type voltage to the heart and prior to the monitoring of the heart action. The deflation may be only partial in the event that the heart action is monitored via sensor electrodes 84 and EKG processing circuitry 86. The deflation may be greater where the cardiac activity is determined via a conventional EKG device separate from balloon 60 and electrodes 84.

To further instill a regular heart beat, a pacemaker type periodic voltage is produced by a generator 96 included, together with generator 92, in voltage source 68. The pacemaker type voltage is applied to the patient's heart via contacts or electrodes 64 upon an inflation of balloon 60 sufficient to ensure electrically conductive engagement between the heart tissues and the electrodes. Control unit 80 regulates the pressurization of balloon 60 via valve device 74 and pressure source 78.

Figure 9:
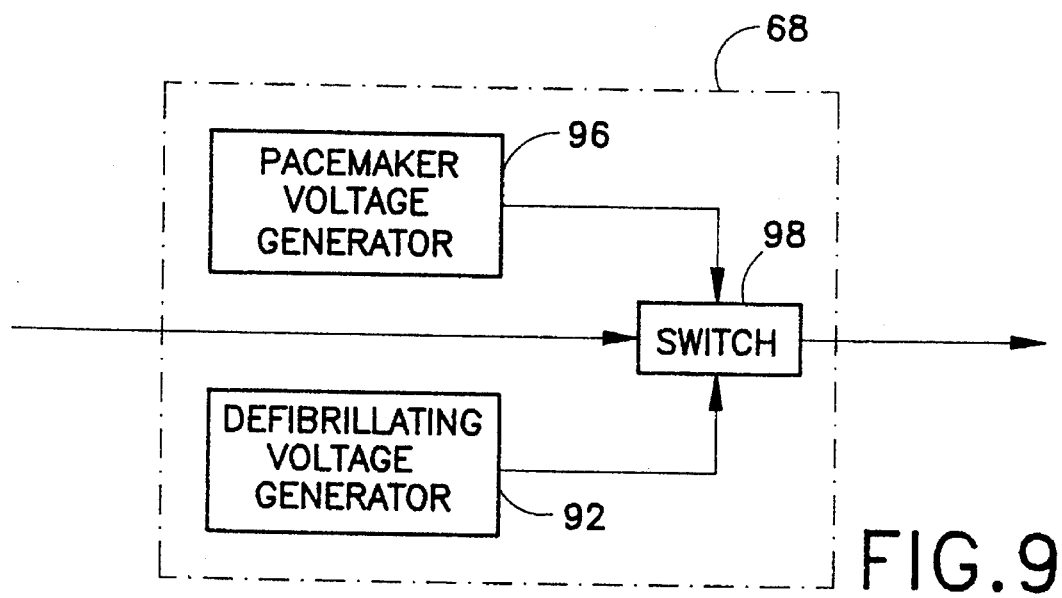
FIG. 9 is a block diagram showing details of the voltage source illustrated in FIG. 8.

The pacemaker type voltage may be applied after a defibrillating procedure as described hereinabove and after periodic cuff inflation to strengthen the heart beat. Control unit 80 determines by the activation of a switch 98 (FIG. 9) whether a defibrillating type voltage or a pacemaker voltage is applied to the cardiac tissues.

As described hereinabove with reference to FIG. 4, the insertion of balloon 60 into the intrapericardial space may be implemented using hypodermic type needle 34. Needle 34 is inserted through a skin surface and into the intrapericardial space, balloon 60 being injected in the collapsed configuration through the needle into the intrapericardial space. As further discussed hereinabove with reference to FIGS. 7A–7C, dilating device 52 may be provided for facilitating the insertion of balloon 60 into the intrapericardial space. Needle 50 is partially inserted through the skin surface and into the intrapericardial space and a distal end portion of dilating device 52 is placed into the intrapericardial space via the needle upon the partial insertion thereof into the intrapericardial space. Dilating device 52 is subsequently expanded and balloon 60 inserted into the intrapericardial space through the expanded dilating device.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An intrapericardial assist device comprising:

an electrode carrier having a surface for contacting a patient's heart in an intrapericardial space;

electrical contact means disposed on said surface for conducting electrical energy to the heart upon an insertion of said electrode carrier into the intrapericardial space;

means operatively connected to said contact means for supplying electrical energy to said contact means; and means connected to said electrode carrier for maintaining said surface in contact with the patient's heart, said electrode carrier being a collapsible member which has a configuration of a slotted cuff in an expanded configuration, said electrode carrier having a predetermined size and shape in said expanded configuration so that said electrode carrier is disposable in the intrapericardial space in juxtaposition to the patient's heart.

2. The device defined in claim 1, further comprising spring means connected to said electrode carrier for automatically unfurling said carrier from a folded collapsed configuration to said expanded configuration.

3. The device defined in claim 2 wherein said spring means includes an elongate rib element.

4. The device defined in claim 1, further comprising sensing means disposed in part on said carrier for generating an electrocardiograph of the patient's heart activity.

5. An intrapericardial assist device comprising:

an electrode carrier having a surface for contacting a patient's heart in an intrapericardial space;

electrical contact means disposed on said surface for conducting electrical energy to the heart upon an insertion of said electrode carrier into the intrapericardial space;

means operatively connected to said contact means for supplying electrical energy to said contact means; and means connected to said electrode carrier for maintaining said surface in contact with the patient's heart;

said electrode carrier having the form of a balloon, said means for maintaining including inflation means operatively connected to said electrode carrier for inflating said electrode carrier from a folded collapsed configuration to an unfolded expanded configuration.

6. The device defined in claim 5, further comprising spring means connected to said electrode carrier for automatically unfurling said carrier from said folded collapsed configuration to said unfolded expanded configuration.

7. The device defined in claim 6 wherein said spring means includes an elongate rib element.

8. The device defined in claim 5 wherein said inflation means includes means for automatically and periodically inflating and alternately deflating said balloon upon a disposition thereof into said intrapericardial space.

9. The device defined in claim 5, further comprising sensing means disposed in part on said carrier for generating an electrocardiograph of the patient's heart activity.

10. A surgical method for reactivating a malfunctioning heart, comprising the steps of:

providing an inflatable balloon in a collapsed configuration, said balloon being provided with an electrode on a surface adapted for contact with a patient's heart;

inserting said balloon into an intrapericardial space about the patient's heart;

upon insertion of said balloon into the intrapericardial space, inflating said balloon to place said electrode in electrically conductive contact with the heart of the patient; and upon inflation of said balloon, conducting a voltage through the electrode to the patient's heart.

11. The method defined in claim 10 wherein said voltage is a defibrillating voltage, further comprising the steps of:

upon completion of said step of conducting, monitoring heart action via an EKG device for a predetermined period; and upon a determination that the heart has started with an inadequate strength, inflating said balloon in synchronism with a heart contraction to place a compressive pressure on the heart to thereby increase pumping action.

12. The method defined in claim 11, further comprising the step of at least partially deflating said balloon upon completion of said step of conducting and prior to said step of monitoring.

13. The method defined in claim 11, further comprising the steps of:

generating a pacemaker type periodic voltage;

applying said periodic voltage to the heart via said electrode upon completion of said step of inflating said balloon in synchronism with a heart contraction to place a compressive pressure on the heart; and maintaining said balloon in an inflated state during said step of applying to maintain said electrode in electrically conductive contact with the heart of the patient.

14. The method defined in claim 10, further comprising the steps of generating a pacemaker type periodic voltage, said step of conducting including the step of applying said periodic voltage to the heart via said electrode; and maintaining said balloon in an inflated state during said step of applying to maintain said electrode in electrically conductive contact with the heart of the patient.

15. The method defined in claim 10 wherein said step of inserting includes the steps of providing a hypodermic type needle, inserting said needle through a skin surface and into said intrapericardial space, and injecting said balloon in said collapsed configuration into said intrapericardial space.

16. The method defined in claim 10, further comprising the step of deflating said balloon upon completion of said step of inflating, also comprising the step of again inflating said balloon upon deflation thereof.

17. The method defined in claim 10, further comprising the step of periodically inflating said balloon upon completion of said step of conducting.

18. The method defined in claim 10 wherein said balloon has an arcuate cuff configuration in an inflated configuration, further comprising the step of placing said balloon at least partially around the heart in said intrapericardial space upon completion of said step of inserting.

19. The method defined in claim 10, further comprising the steps of providing a hypodermic type needle and a dilating device, said step of inserting including the steps of partially inserting said needle through a skin surface and into said intrapericardial space and placing a distal end portion of said dilating device into said intrapericardial space via said needle upon the partial insertion thereof into said intrapericardial space, also comprising the step of expanding said dilating device upon the insertion of the distal end portion thereof into said intrapericardial space, said balloon being inserted into said intrapericardial space through the expanded dilating device.

* * * * *